United States Patent
Van Delft et al.

(10) Patent No.: US 9,822,414 B2
(45) Date of Patent: Nov. 21, 2017

(54) IN VITRO METHOD FOR PREDICTING IN VIVO GENOTOXICITY OF CHEMICAL COMPOUNDS

(75) Inventors: Joseph Henri Marie Van Delft, Etterbeek (BE); Joseph Catharina Stephanus Kleinjans, Maastricht (NL); Christina Magkoufopoulou, Norwich (GB); Danyel Gerardus Jacobus Jennen, Elsloo (NL)

(73) Assignees: UNIVERSITEIT MAASTRICHT, Maastricht (NL); ACADEMISCH ZIEKENHUIS MAASTRICHT, Maastricth (NL)

( * ) Notice: Subject to any disclaimer, the term of this patent is extended or adjusted under 35 U.S.C. 154(b) by 143 days.

(21) Appl. No.: 14/117,731

(22) PCT Filed: May 19, 2012

(86) PCT No.: PCT/EP2012/059317
§ 371 (c)(1),
(2), (4) Date: Jan. 27, 2014

(87) PCT Pub. No.: WO2012/156526
PCT Pub. Date: Nov. 22, 2012

(65) Prior Publication Data
US 2014/0194309 A1 Jul. 10, 2014

(30) Foreign Application Priority Data
May 19, 2011 (EP) ..................................... 11166771

(51) Int. Cl.
*C12Q 1/68* (2006.01)
*G01N 33/50* (2006.01)

(52) U.S. Cl.
CPC ....... *C12Q 1/6883* (2013.01); *G01N 33/5014* (2013.01); *G01N 33/5017* (2013.01)

(58) Field of Classification Search
None
See application file for complete search history.

(56) References Cited

U.S. PATENT DOCUMENTS

| 7,683,036 | B2 * | 3/2010 | Esau | C12N 15/111 514/44 R |
| 7,858,608 | B2 * | 12/2010 | Pellicciari | C07J 9/00 514/182 |
| 7,932,244 | B2 * | 4/2011 | Pellicciari | C07J 9/00 514/182 |
| 2005/0158805 | A1 * | 7/2005 | Purcell | G01N 33/5014 435/7.21 |
| 2009/0269744 | A1 | 10/2009 | Krause et al. | |
| 2010/0120893 | A1 * | 5/2010 | Sah | C12N 15/111 514/44 A |
| 2011/0166043 | A1 | 7/2011 | Nagy et al. | |
| 2011/0250606 | A1 | 10/2011 | Kleinjans et al. | |
| 2012/0108444 | A1 | 5/2012 | Philibert et al. | |
| 2012/0122727 | A1 | 5/2012 | Kleinjans et al. | |

FOREIGN PATENT DOCUMENTS

| WO | 2007048978 A2 | 5/2007 |
| WO | 2009064321 A2 | 5/2009 |
| WO | 2010070059 A1 | 6/2010 |
| WO | 2010129354 A2 | 11/2010 |
| WO | 2011012665 A1 | 2/2011 |
| WO | 2012156526 A1 | 11/2012 |

OTHER PUBLICATIONS

Newton et al. Environ Health Perspect 112:420-422 (2004).*
Collins et al., Generation and initial analysis of more than 15,000 full-length human and mouse cDNA sequences, PNAS, Dec. 24, 2002, vol. 99, No. 26, pp. 16899-16903, plus Supporting information, pp. 1-78.
PCT International Search Report, PCT/EP2012/059317, dated Sep. 3, 2012.
Database Entrez Gene (Online) NCBI, Oct. 29, 2011, HOGA1 r-hydroxy-2-oxoglutarate aldolase 1, XP002662622.
Database Entrez Gene (Online) NCBI, Jun. 20, 2009, Hypothetical protein LOC100131914, XP002662621.
Dumitriu et al., Human Dendritic Cells Produce TGF-1 under the Influence of Lung Carcinoma Cells and Prime the Differentiation of CD4+CD25+Foxp3+ Regulatory T Cells, Journal of Immunology, Mar. 1, 2009, pp. 2795-2807, vol. 182, No. 5.
Magkoufopoulou et al., Comparison of phenotypic and transcriptomic effects of false-positive genotoxins, true genotoxins and non-genotoxins using HepG2 cells, Mutagenesis, Sep. 1, 2011, pp. 593-604, vol. 26, No, 5, IRL Press, Oxford, GB.
Van Delft et al., Discrimination of genotoxic from non-genotoxic carcinogens by gene expression profiling, Carcinogenesis, Feb. 1, 2004, pp. 1265-1276, vol. 25, No. 7, Oxford University Press, GB.
PCT International Written Opinion, PCT/EP2012/059317, dated Sep. 3, 2012.
PCT International Preliminary Report on Patentability, PCT/EP2012/059317, dated Nov. 19, 2013.

* cited by examiner

*Primary Examiner* — James Martinell
(74) *Attorney, Agent, or Firm* — TraskBritt, P.C.

(57) ABSTRACT

The invention is in the field of genomics and it provides an in vitro method for predicting whether a compound is genotoxic in vivo. In particular, the invention provides a method for predicting the in vivo genotoxicity of a compound comprising the steps of performing an Ames test on the compound and determining if the result is positive or negative, followed by a step wherein the gene expression of at least 3 genes is determined in a HepG2 cell, compared to a reference value and predicting that the compound is in vivo genotoxic if the expression level of more than 2 of the genes is above a reference value.

5 Claims, No Drawings

IN VITRO METHOD FOR PREDICTING IN VIVO GENOTOXICITY OF CHEMICAL COMPOUNDS

FIELD OF THE INVENTION

The invention is in the field of genomics and it provides an in vitro method for predicting whether a compound is genotoxic in vivo.

BACKGROUND OF THE INVENTION

Cancer is one of the leading causes of death accounting for 13% of all deaths worldwide in 2004 according to the World Health Organization. In 2007 and 2008, cancer was ranked the second cause of death accounting for 23% and 26% of total deaths, in the US and Europe respectively (1, 2). Cancer is a very complicated and yet not fully understood disease, nevertheless, two causal factors for its development is appreciated. The first is the presence of specific gene mutations genetically inherited or endogenously induced, e.g. BRCA1 and BRCA2 mutations are considered responsible for breast cancer (3). The second is exposure to exogenous carcinogenic factors, such as the link between tobacco smoke and lung cancer (4). The molecular mechanism of tumor formation after carcinogenic exposure frequently comprises the induction of DNA mutations by the carcinogen or its metabolites. If mutations occur within genes responsible for cell proliferation or survival, the cells may become malignant (5). Cellular transformation to a tumor cell may also be caused through a variety of mechanisms (production of reactive oxygen species, immunosuppression, peroxisome proliferation etc.) which do not necessarily involve DNA damage. Consequently, carcinogens are classified as genotoxic (GTX) or non-genotoxic (NGTX) (5). Since almost all GTX compounds are carcinogenic, it is important, in particular for regulatory purposes, to evaluate the genotoxic potential of chemicals to which humans are exposed, and therefore to discriminate between GTX and NGTX compounds.

The most commonly used assay, the *Salmonella typhimurium* test, for evaluating mutagenic properties of chemicals in vitro was developed in 1975 by Bruce N. Ames (6). Subsequently, several in vitro assays were developed aiming at assessing genotoxic properties of chemicals in mammalian cellular models and are accepted by the regulatory authorities. However, the conventional in vitro test battery consisting of a bacterial mutation assay [Ames assay], mammalian micronuclei [MN], chromosomal aberration [CA] and mouse lymphoma assays [MLA]) often fails to correctly predict in vivo genotoxic and carcinogenic potential of compounds, even reaching a 50% false positive rate in some cases (7).

Depending on the intended use of the chemicals and the purpose of the assessment, regulatory authorities may require the in vivo evaluation of genotoxic and carcinogenic properties in rodents, especially for chemicals that are genotoxic in vitro (EC 1907/2006) and/or intended for human use (8). As a consequence of the high false positive rate of these in vitro assays, a high number of unnecessary animal experiments are performed each year. Next to its limited relevance for human health, the use of experimental animals inflicts considerable costs and raises ethical issues.

In cases where animal testing is not required after positive outcomes of in vitro assays (Globally Harmonized System of Classification and Labelling of Chemicals (GHS), 3rd revised edition, UN, 2009), false positive in vitro results cause wrong chemical classifications.

Overall, a more reliable in vitro assay for predicting in vivo genotoxicity is urgently required.

SUMMARY OF THE INVENTION

The aim of this study was to develop an in vitro transcriptomics-based prediction method for in vivo genotoxicity.

The invention provides an in vitro method for predicting whether a compound is genotoxic in vivo. In particular, the invention provides a method for predicting the in vivo genotoxicity of a compound comprising the steps of performing an Ames test for the compound and determining if the result is positive or negative, followed by a step wherein the gene expression level of at least 3 genes is determined in at least one HepG2 cell, compared to a reference value and predicting that the compound is in vivo genotoxic if the expression level of at least two genes is above the predetermined reference value.

More in particular, we found that in vivo genotoxicity could be predicted by a method for predicting the in vivo genotoxicity of a compound comprising the steps of
a. performing an Ames test on the compound and determining if the compound is Ames positive or Ames negative,
b. providing a HepG2 cell
c. exposing the HepG2 cell for a period of time between 12 and 48 hours to said compound,
d. if the compound is Ames positive, determining the level of expression of a first gene set comprising at least genes NR0B2, PWWP2B and LOC100131914,
e. if the compound is Ames negative, determining the level of expression of a second gene set, comprising at least genes SLC40A1, PNMA6A and C10orf65
f. Comparing the level of expression of the first gene set or the second gene set to a predetermined reference value,
wherein the compound is predicted to be in vivo genotoxic if the expression level of at least 2 genes exposed to the compound are above their predetermined reference values.

This method appeared to be superior to the conventional methods as further detailed herein.

DETAILED DESCRIPTION OF THE INVENTION

In this study we aimed at developing an alternative in vitro transcriptomics-based method for predicting in vivo genotoxic properties of chemicals.

This novel approach for the prediction of in vivo genotoxicity results in an improved accuracy when compared to each of the conventional in vitro genotoxicity assays or to the combination of Ames assay with the other conventional in vitro methods.

We surprisingly found that the accuracy and sensitivity of the classical Ames test could be greatly improved when the results were combined with a gene expression assay as described herein.

In particular, the invention relates to a method for predicting the in vivo genotoxicity of a compound comprising the steps of
a. performing an Ames test on the compound and determining if the compound is Ames positive or Ames negative,
b. providing a HepG2 cell c. exposing the HepG2 cell for a period of time between 12 and 48 hours to said compound,
d. if the compound is Ames positive, determining the level of expression of a first gene set comprising at least genes NR0B2, PWWP2B and LOC100131914,
e. if the compound is Ames negative, determining the level of expression of a second gene set, comprising at least genes SLC40A1, PNMA6A and C10orf65
f. Comparing the level of expression of the first gene set or the second gene set to a predetermined reference value, wherein the compound is predicted to be in vivo genotoxic if the expression level of at least 2 genes exposed to the compound are above their predetermined reference values.

The term "in vivo genotoxicity" is intended to mean the ability of a chemical to cause DNA damage in vivo, as determined by a positive result in at least one in vivo genotoxicity assay, including but not limited to the MN and CA assays as described in the OECD guidelines of testing of chemicals, Test No 474 and Test No 475, respectively.

The phrase "the expression level of at least 2 genes exposed to the compound" is intended to mean "the expression level of at least 2 genes within said first or second gene set".

The expression "at least 2 genes" in the context of the testing of 3 genes is intended to mean "2" or "3".

The term "Ames test" is intended to mean the bacterial reverse mutation assay as described by the OECD guideline of testing for chemicals: Test No. 471.

The term "Ames positive" is intended to refer to a positive mutagenic result in the Ames test.

The term "Ames negative" is intended to refer to a non-mutagenic result in the Ames test The term "HepG2 cell" is intended to mean the cell of human hepatocellular carcinoma origin with ATCC no. HB-8065, with a karyotype as described by Wong et. al (Wong N, Lai P, Pang E, Leung T W, Lau J W, Johnson P J. A comprehensive karyotypic study on human hepatocellular carcinoma by spectral karyotyping. Hepatology. 2000 November; 32 (5):1060-8).

The term "determining the level of expression" is intended to mean the quantitative measurement of mRNA molecules expressed by a certain gene present in HepG2 cells. Such mRNA levels may be determined by several methods known in the art such as microarray platforms, Reverse-Transcriptase Polymerase Chain Reaction (RT-PCR), and deep sequencing.

The term "reference compound" is intended to mean a compound for which results are available in the Ames test and an in vivo genotoxicity assay.

The term "Ames positive in vivo genotoxic reference compound" is intended to mean a compound with mutagenic results in the Ames test and the ability to cause DNA damage in vivo, as determined by a positive result in at least one in vivo genotoxicity assay, including but not limited to the MN and CA assays as described in the OECD guidelines of testing of chemicals, Test No 474 and Test No 475, respectively.

The term "Ames positive in vivo non-genotoxic reference compound" is intended to mean compound with mutagenic results in the Ames test and lack of the ability to cause DNA damage in vivo, as determined by a negative result in all the in vivo genotoxicity assays that the compound has been tested, including but not limited to the MN and CA assays, as described in the OECD guidelines of testing of chemicals, Test No 474 and Test No 475, respectively.

The term "Ames negative in vivo genotoxic reference compound" is intended to mean compound with non-mutagenic results in the Ames test and the ability to cause DNA damage in vivo, as determined by a positive result in at least one in vivo genotoxicity assay, including but not limited to the MN and CA assays as described in the OECD guidelines of testing of chemicals, Test No 474 and Test No 475, respectively.

The term "Ames negative in vivo non-genotoxic reference compound" is intended to mean compound with non-mutagenic results in the Ames test and lack of the ability to cause DNA damage in vivo, as determined by a negative result in all the in vivo genotoxicity assays that the compound has been tested, including but not limited to the MN and CA assays, as described in the OECD guidelines of testing of chemicals, Test No 474 and Test No 475, respectively.

The term "reference value" is intended to refer to the level of mRNA expression of a certain gene in HepG2 cells not exposed to a test compound. This reference value is used as a reference to which the expression level of the gene in HepG2 cell(s) after exposure to a test compound is compared.

The term "mean expression level" is intended to mean the average of the obtained expression levels for a single gene from all conducted biological and/or technical replicates.

The term "about 24 hours" is to be interpreted as meaning 24 hours plus or minus 2 hours, preferably plus or minus 1 hour, most preferably plus or minus half an hour.

When the method according to the invention was performed using a first gene set consisting of the genes NR0B2, PWWP2B, and LOC100131914 for the Ames positive compounds, an accurate prediction was obtained in about 80% of the cases.

When the method according to the invention was performed using a second gene set consisting of genes SLC40A1, PNMA6A and C10orf65 for the Ames negative compounds, an accurate prediction was obtained in about 90% of the cases.

The results obtained with the method according to the invention could even be improved when additional genes were included in the analysis. When the first gene set for the Ames positive compounds as mentioned above was supplemented with at least one gene selected from the group consisting of genes CEACAM1, SLC27A1, TTR, UBE2E2, NAT8, GMFG, RBPMS, C10orf10, PROSC, TBC1D9, OR10H1, APOM, C1orf128, AVEN, ZNRF3 and SNORD8, the results improved.

The invention therefore relates to a method as described above wherein the first gene set additionally comprises at least one gene selected from the group consisting of genes CEACAM1, SLC27A1, TTR, UBE2E2, NAT8, GMFG, RBPMS, C10orf10, PROSC, TBC1D9, OR10H1, APOM, C1orf128, AVEN, ZNRF3 and SNORD8.

The results obtained with a method according to the invention could also be improved when additional genes were added to the second set. When the second gene set for the Ames negative compounds as mentioned above was supplemented with at least one gene selected from the group consisting of genes SGK1, SLC64A, ANXA6, BTD, FGA, NDUFA10, NFATC3, MTMR15, ANAPC5, ZNF767, SCRN2 and GSTK1, the results improved.

The invention therefore relates to a method as described above wherein the second gene set additionally comprises at least one gene selected from the group consisting of genes SGK1, SLC64A, ANXA6, BTD, FGA, NDUFA10, NFATC3, MTMR15, ANAPC5, ZNF767, SCRN2 and GSTK1.

A reference value for a gene may be empirically determined by methods known in the art. The reference values may be varied depending on the desire to either improve the sensitivity of the assay or the specificity. A skilled person in the art will know the metes and bounds of choosing a reference value.

In a preferred embodiment, a reference value for a particular gene is obtained by determining the expression level of that particular gene in the presence and absence of a genotoxic compound. The ratio between the expression level in the presence and the absence of the genotoxic compound is termed the GTX ratio. Thereafter, the expression level of that particular gene in the presence and absence of a non-genotoxic compound is determined. The ratio between the expression level in the presence and the absence of the non-genotoxic compound is termed the non-GTX ratio. The average value of the log 2 of the GTX ratio and the non-GTX ratio is a suitable reference value. The reliability of the reference value may be increased by determining the GTX- and non-GTX ratios in the presence and absence of multiple genotoxic and non-genotoxic compounds.

Hence, the invention also relates to a method as described above wherein the predetermined reference value for a particular gene is calculated as the mean of the log 2 of the ratios of the expression level said gene in the presence and absence of at least one genotoxic compound and at least one non-genotoxic reference compound.

A preferred criterion for predicting a compound as in vivo genotoxic is as follows.

First, the expression level of each of these 3 genes NR0B2, PWWP2B, and LOC100131914 as described above is determined in a HepG2 cell in the presence and absence of the compound. The ratio between the expression levels in the presence and absence of the compound is then determined. The log 2 value of this ratio is then compared with the reference values shown in table 1.

If the log 2 value of the ratio of the expression level of at least two of the three genes in cells exposed to the compound is above the reference value, then the compound is predicted to be in vivo genotoxic. If log 2 value of the ratio of the expression level of at least two of the three genes in cell(s) exposed to the compound are below the reference value, then the compound is predicted to be in vivo non-genotoxic.

Hence, the invention also relates to a method as described above wherein the predetermined reference value for the gene is taken from table 1.

TABLE 1

Genes and their reference values.

| EntrezGene ID | Gene Symbol | Gene Name/function | Reference value |
|---|---|---|---|
| 8431 | NR0B2 | nuclear receptor subfamily 0, group B, member 2 | −0.099 |
| 170394 | PWWP2B | PWWP domain containing 2B | −0.071 |
| 100131914 | LOC100131914 | hypothetical protein LOC100131914 (custom CDF version 11), identical with LOC100505880 (custom CDF version 14) | −0.054 |
| 634 | CEACAM1 | Receptor ligand | 0.1795 |
| 1183 | CLCN4 | Voltage-gated ion-channel | −0.014 |
| 2009 | EML1 | Generic phosphatase | −0.1825 |
| 7325 | UBE2E2 | Generic enzyme | 0.006 |

TABLE 1-continued

Genes and their reference values.

| EntrezGene ID | Gene Symbol | Gene Name/function | Reference value |
|---|---|---|---|
| 8975 | USP13 | Generic protease | 0.046 |
| 9535 | GMFG | Generic binding protein | −0.0125 |
| 11212 | PROSC | Generic protein | −0.0445 |
| 7276 | TTR | Generic binding protein | −0.2465 |
| 9027 | NAT8 | Generic enzyme | −0.267 |
| 11030 | RBPMS | Generic binding protein | −0.0495 |
| 11067 | C10orf10 | Generic protein | 0.0355 |
| 23158 | TBC1D9 | Generic protein | −0.163 |
| 29916 | SNX11 | Generic binding protein | −0.0575 |
| 54538 | ROBO4 | Generic receptor | 0.104 |
| 54880 | BCOR | Generic binding protein | −0.1415 |
| 6092 | ROBO2 | Generic receptor | 0.081 |
| 6725 | SRMS | Protein kinase | −0.0775 |
| 26539 | OR10H1 | GPCR | 0.0455 |
| 27010 | TPK1 | Generic kinase | 0 |
| 64115 | C10orf54 | Generic receptor | 0.0405 |
| 319103 | SNORD8 | RNA | −0.0105 |
| 414918 | FAM116B | Generic protein | 0.0655 |
| 55937 | APOM | Transporter | −0.163 |
| 56675 | NRIP3 | Generic binding protein | 0.0465 |
| 57095 | C1orf128/PITHD1 | Generic protein | 0.1155 |
| 57099 | AVEN | Generic binding protein | 0.148 |
| 60677 | BRUNOL6 | Generic binding protein | 0.086 |
| 84133 | ZNRF3 | Generic binding protein | −0.3185 |
| 146227 | BEAN | Generic binding protein | 0.119 |
| 376497 | SLC27A1 | Generic enzyme | −0.037 |

Similarly, when the second gene set consisting of the three genes SLC40A1, PNMA6A and C10orf65 is used, a preferred criterion for predicting an Ames negative compound as in vivo genotoxic is as follows.

First, the expression level of each of these 3 genes in a HepG2 cell is determined in the presence and absence of the compound. The ratio between the expression levels in the presence and absence of the compound is then determined. The log 2 value of this ratio is then compared with the reference values shown in table 2.

If the log 2 value of the ratio of the expression level of at least two of the three genes in cells exposed to the compound is above the reference value, then the compound is predicted to be in vivo genotoxic. If log 2 value of the ratio of the expression level of at least two of the three genes in cell(s) exposed to the compound are below the reference value, then the compound is predicted to be in vivo non-genotoxic.

Hence, the invention relates to a method as described above wherein the predetermined reference value for the gene is taken from table 2.

TABLE 2

Genes and their reference values.

| Entrez Gene ID | Gene Symbol | Gene name | Reference Value |
|---|---|---|---|
| 30061 | SLC40A1 | solute carrier family 40 (iron-regulated transporter), member 1 | 0.329 |
| 84968 | PNMA6A | paraneoplastic antigen like 6A | 0.251 |
| 112817 | C10orf65 | chromosome 10 open reading frame 65, HOGA1 (4-hydroxy-2-oxoglutarate aldolase 1) | 0.146 |
| 309 | ANXA6 | Generic binding protein | 0.1655 |
| 337 | APOA4 | Receptor ligand | 0 |
| 686 | BTD | Generic enzyme | 0.037 |
| 1939 | LGTN | Generic receptor | 0.0275 |

TABLE 2-continued

Genes and their reference values.

| Entrez Gene ID | Gene Symbol | Gene name | Reference Value |
|---|---|---|---|
| 3267 | AGFG1 | Generic binding protein | −0.086 |
| 4705 | NDUFA10 | Generic enzyme | 0.038 |
| 4775 | NFATC3 | Transcription factor | 0.159 |
| 9373 | PLAA | Generic binding protein | −0.057 |
| 22909 | MTMR15 | Generic binding protein | 0.0755 |
| 51433 | ANAPC5 | Generic enzyme | 0.0265 |
| 64969 | MRPS5 | Generic binding protein | 0.0845 |
| 79970 | ZNF767 | Generic protein | 0.0985 |
| 373156 | GSTK1 | Generic enzyme | 0.0355 |
| 2243 | FGA | Generic binding protein | −0.0205 |
| 6446 | SGK1 | Protein kinase | 0.1975 |
| 6532 | SLC6A4 | Transporter | 0.0535 |
| 90507 | SCRN2 | Generic protease | 0.0405 |
| 200014 | CC2D1B | Generic protein | 0.0165 |
| 648921/ 288921 | LOC648921/ LOC283693 | — | −0.048 |

As an illustrative example only, the following simplified model is provided for the calculation of a reference value.

First the expression ratio of gene A is calculated. Therefore, the relative expression level of gene A is determined in the presence and absence of genotoxic compound Z. The expression level in the presence of compound Z is found to be 6 times higher than in its absence. It is then concluded that the GTX ratio of gene A is log 2 of 6=2.58. The expression level of gene A in the presence of non-genotoxic compound Y is found to be 2 times higher than in its absence. It is then concluded that the non-GTX ratio of gene A is log 2 of 2=1. A suitable reference value for gene A is than the average between the GTX ratio and the non-GTX ratio, in this example (2.58+1)/2=1.79.

Instead of a GTX ratio obtained with only one genotoxic compound, it may be advantageous to obtain several GTX ratios with different genotoxic compounds and calculate an average GTX ratio. The same may apply mutatis mutandis for non-GTX ratios.

When more than 3 genes are used in the method according to the invention, the reliability of the method may even be further improved when the criterion for genotoxicity is that (apart from the criterion that at least two out of three genes are above their reference value) more than half of the number of genes exposed to the compound are above their predetermined reference values.

Hence, the invention also relates to a method as described above wherein the compound is predicted to be in vivo genotoxic if the expression level of more than half of the number of genes exposed to the compound are above their predetermined reference values.

In a preferred embodiment, the step of comparing the level of expression of the first gene set or the second gene set to a predetermined reference value, is performed by a computer program.

A computer program particularly suited for this purpose is PAM (Prediction Analysis for Microarrays) or Support Vector Machines (SVM).

Representative examples of the accuracy, sensitivity and specificity of the method according to the invention are presented in Table 3.

TABLE 3

Comparison of the performance of Ames test, in vitro test battery and a method according to the invention.

|  | Ames | in vitro test battery[1] | Invention |
|---|---|---|---|
| Accuracy | 79.0% | 67.7% | 84.4% |
| Sensitivity | 78.3% | 95.7% | 85.5% |
| Specificity | 79.5% | 51.3% | 83.8% |

[1]positive result in at least one test, i.e. Ames, MLA, MN and/or CA.

The method according to the invention showed a clear improvement in comparison to methods of the prior art in regard to the accuracy and the specificity. A comparison of the results obtained by the method according to the invention and by conventional in vitro assays, is presented in Table 3.

When a method according to the invention was performed on a set of 62 compounds, the following results were obtained (Table 4): The raw data underlying table 4 are presented in tables 4A-4D.

TABLE 4

Class prediction results using the method of the invention

| Compound | Prediction | Compound | Prediction |
|---|---|---|---|
| 2AAF | GTX+ | ABP | GTX |
| AFB1 | GTX | AZA | GTX |
| APAP | NGTX | BZ | GTX |
| BaP | GTX | Cb | GTX |
| DES | GTX | cisPt | GTX |
| DMBA | GTX+ | CP | GTX |
| DMN | GTX+ | DEN | GTX |
| MMC | NGTX+ | ENU | GTX |
| pCres | GTX | FU | NGTX+ |
| Ph | GTX | IQ | GTX |
| TBTO | GTX | MOCA | GTX |
| VitC | GTX | 2-Cl | GTX+ |
| 2CMP | NGTX | Anis | GTX |
| 4AAF | NGTX+ | ASK | NGTX |
| 8HQ | GTX+ | BDCM | NGTX |
| ampC | NGTX | CAP | NGTX+ |
| AnAc | NGTX | CCl4 | NGTX+ |
| CsA | NGTX | Cou | NGTX |
| Cur | NGTX | DDT | NGTX |
| DEHP | NGTX | DZN | NGTX |
| Diclo | NGTX | EthylB | NGTX |
| Dman | NGTX | EuG | NGTX+ |
| E2 | NGTX | HCH | NGTX |
| EtAc | GTX | NBZ | NGTX+ |
| NPD | NGTX+ | PCP | NGTX |
| PhB | NGTX | Prog | NGTX |
| Phen | NGTX | Sim | NGTX |
| Que | NGTX | TCE | NGTX |
| Res | NGTX |  |  |
| RR | GTX |  |  |
| Sulfi | NGTX |  |  |
| TCDD | NGTX |  |  |
| TPA | NGTX |  |  |
| WY | NGTX |  |  |

GTX: the compound is predicted genotoxic;
NGTX: the compound is predicted non-genotoxic;
Results indicated with bold and underlined letters indicate misclassification;
Results labeled + indicate that two of the three replicates were classified in the indicated class.

TABLE 4A

Log2 treatment: control ratios obtained in triplicate experiments with Ames positive compounds.

|  | NR0B2 | PWWP2B | LOC100505880 |
|---|---|---|---|
| 2AAF | 0.042 | −0.045 | −0.103 |
| 2AAF | −0.673 | −0.14 | −0.643 |

TABLE 4A-continued

Log2 treatment: control ratios obtained in triplicate experiments with Ames positive compounds.

| | NR0B2 | PWWP2B | LOC100505880 |
|---|---|---|---|
| 2AAF | 0.472 | 0.042 | 0.579 |
| ABP | 0.806 | 0.442 | 0.65 |
| ABP | 0.211 | 0.047 | 0.088 |
| ABP | 0.217 | 0.264 | −0.072 |
| AFB1 | 0.605 | 0.098 | 0.281 |
| AFB1 | 1.482 | 0.275 | 0.774 |
| AFB1 | 0.548 | 0.088 | 0.534 |
| AZA | 1.473 | 0.536 | 1.541 |
| AZA | 0.232 | 0.044 | 0.022 |
| AZA | 0.893 | −0.035 | 1.33 |
| BaP | 1.322 | 0.119 | 1.086 |
| BaP | 1.8 | 0.439 | 1.208 |
| BaP | 0.592 | 0.105 | 0.877 |
| BZ | 1.254 | 0.013 | 0.217 |
| BZ | 0.556 | −0.137 | 0.523 |
| BZ | 0.916 | 0.255 | −0.087 |
| Cb | 1.254 | 0.399 | 1.036 |
| Cb | 0.671 | −0.133 | 0.803 |
| Cb | 0.519 | 0.145 | 0.483 |
| cisPt | 0.367 | 0.095 | 0.35 |
| cisPt | 1.545 | −0.147 | 0.602 |
| cisPt | 0.467 | −0.18 | 0.166 |
| CP | −0.404 | 0.042 | −0.031 |
| CP | 0.276 | −0.221 | −0.01 |
| CP | 0.039 | 0.073 | 0.139 |
| DEN | 0.689 | 0.087 | 0.823 |
| DEN | 0.245 | 0.095 | 0.448 |
| DEN | −0.262 | 0.056 | −0.022 |
| DMBA | 0.064 | −0.155 | 0.08 |
| DMBA | −0.116 | 0.088 | −0.059 |
| DMBA | −0.076 | −0.102 | −0.025 |
| DMN | −0.173 | −0.011 | 0.222 |
| DMN | −1.832 | −0.368 | −0.518 |
| DMN | −0.051 | −0.304 | 0.321 |
| ENU | 0.424 | 0.01 | 0.088 |
| ENU | 0.901 | 0.06 | 0.382 |
| ENU | 1.056 | 0.11 | −0.192 |
| FU | 0.781 | 0.256 | 0.583 |
| FU | −0.197 | 0.175 | −0.067 |
| Fu | −0.457 | 0.008 | −0.218 |
| IQ | 0.847 | 0.188 | 3.101 |
| IQ | 0.627 | −0.003 | 2.784 |
| IQ | −0.396 | −0.052 | 2.082 |
| MMC | 0.071 | −0.106 | −0.208 |
| MMC | −0.308 | −0.232 | −0.256 |
| MMC | 0.38 | 0.022 | 0.595 |
| MOCA | 0.498 | 0.047 | 0.088 |
| MOCA | 0.957 | 0.134 | 0.143 |
| MOCA | 0.484 | 0.259 | −0.424 |
| Paracres | 1.286 | 0.271 | −0.41 |
| Paracres | 1.877 | 0.072 | 0.437 |
| Paracres | 1.893 | 0.384 | 0.487 |
| 2-Cl | 0.881 | 0.564 | −0.222 |
| 2-Cl | 0.162 | 0.197 | −0.041 |
| 2-Cl | −0.623 | 0.058 | −0.47 |
| 2CMP | −1.551 | −0.214 | −1.088 |
| 2CMP | −1.683 | −0.23 | −1.225 |
| 2CMP | −1.227 | −0.031 | −0.867 |
| 4AAF | −0.04 | −0.524 | −0.217 |
| 4AAF | −0.278 | −0.086 | −0.295 |
| 4AAF | −0.088 | 0.002 | −0.101 |
| 8HQ | −0.007 | 0.014 | −0.34 |
| 8HQ | −0.753 | −0.165 | −0.572 |
| 8HQ | 0.249 | −0.069 | 0.558 |
| Anis | 0.886 | 0.013 | 1.084 |
| Anis | 0.751 | 0.076 | 0.697 |
| Anis | −0.076 | 0.253 | 0.288 |
| NPDhigh | −0.277 | 0.011 | −0.119 |
| NPDhigh | −0.621 | −0.153 | −0.365 |
| NPDhigh | 0.1 | −0.238 | 0.008 |
| PhB | 0.352 | −0.169 | −0.154 |
| PhB | −0.176 | −0.272 | −0.38 |
| PhB | −0.407 | −0.154 | −0.303 |
| Que | −0.635 | −0.206 | 0.062 |
| Que | −0.69 | −0.437 | −0.337 |
| Que | −3.709 | −0.113 | −0.727 |
| reference value | −0.099 | −0.071 | |

TABLE 4B

Determination of GTX or NGTX status according to a method of the invention wherein a compound is scored as GTX when at least two out of three genes are above the reference value. Plus sign indicates a value above the reference value, minus sign indicates a value below the reference value.

| Compound | Standard | NR0B2 | PWWP2B | LOC100505880 | At least ⅔ genes +? | Average result over three measurements |
|---|---|---|---|---|---|---|
| 2AAF | GTX | + | + | − | GTX | GTX |
| 2AAF | GTX | − | − | − | NGTX | |
| 2AAF | GTX | + | + | + | GTX | |
| ABP | GTX | + | + | + | GTX | GTX |
| ABP | GTX | + | + | + | GTX | |
| ABP | GTX | + | + | − | GTX | |
| AFB1 | GTX | + | + | + | GTX | GTX |
| AFB1 | GTX | + | + | + | GTX | |
| AFB1 | GTX | + | + | + | GTX | |
| AZA | GTX | + | + | + | GTX | GTX |
| AZA | GTX | + | + | + | GTX | |
| AZA | GTX | + | + | + | GTX | |
| BaP | GTX | + | + | + | GTX | GTX |
| BaP | GTX | + | + | + | GTX | |
| BaP | GTX | + | + | + | GTX | |
| BZ | GTX | + | + | + | GTX | GTX |
| BZ | GTX | + | − | + | GTX | |
| BZ | GTX | + | + | − | GTX | |
| Cb | GTX | + | + | + | GTX | GTX |
| Cb | GTX | + | − | + | GTX | |

TABLE 4B-continued

Determination of GTX or NGTX status according to a method of the invention wherein a compound is scored as GTX when at least two out of three genes are above the reference value. Plus sign indicates a value above the reference value, minus sign indicates a value below the reference value.

| Compound | Standard | NR0B2 | PWWP2B | LOC100505880 | At least 2/3 genes +? | Average result over three measurements |
|---|---|---|---|---|---|---|
| Cb | GTX | + | + | + | GTX | |
| cisPt | GTX | + | + | + | GTX | GTX |
| cisPt | GTX | + | − | + | GTX | |
| cisPt | GTX | + | − | + | GTX | |
| CP | GTX | − | + | + | GTX | GTX |
| CP | GTX | + | − | + | GTX | |
| CP | GTX | + | + | + | GTX | |
| DEN | GTX | + | + | + | GTX | GTX |
| DEN | GTX | + | + | + | GTX | |
| DEN | GTX | − | + | + | GTX | |
| DMBA | GTX | + | − | + | GTX | GTX |
| DMBA | GTX | − | + | − | NGTX | |
| DMBA | GTX | + | − | + | GTX | |
| DMN | GTX | − | + | + | GTX | GTX |
| DMN | GTX | − | − | − | NGTX | |
| DMN | GTX | + | − | + | GTX | |
| ENU | GTX | + | + | + | GTX | GTX |
| ENU | GTX | + | + | + | GTX | |
| ENU | GTX | + | + | − | GTX | |
| FU | GTX | + | + | + | GTX | NGTX |
| FU | GTX | − | + | − | NGTX | |
| Fu | GTX | − | + | − | NGTX | |
| IQ | GTX | + | + | + | GTX | GTX |
| IQ | GTX | + | + | + | GTX | |
| IQ | GTX | − | + | + | GTX | |
| MMC | GTX | + | − | − | NGTX | NGTX |
| MMC | GTX | − | − | − | NGTX | |
| MMC | GTX | + | + | + | GTX | |
| MOCA | GTX | + | + | + | GTX | GTX |
| MOCA | GTX | + | + | + | GTX | |
| MOCA | GTX | + | + | − | GTX | |
| Paracres | GTX | + | + | − | GTX | GTX |
| Paracres | GTX | + | + | + | GTX | |
| Paracres | GTX | + | + | + | GTX | |
| 2-Cl | NGTX | + | + | − | GTX | GTX |
| 2-Cl | NGTX | + | + | + | GTX | |
| 2-Cl | NGTX | − | + | − | NGTX | |
| 2CMP | NGTX | − | − | − | NGTX | NGTX |
| 2CMP | NGTX | − | − | − | NGTX | |
| 2CMP | NGTX | − | + | − | NGTX | |
| 4AAF | NGTX | + | − | − | NGTX | NGTX |
| 4AAF | NGTX | − | − | − | NGTX | |
| 4AAF | NGTX | + | + | − | GTX | |
| 8HQ | NGTX | + | + | − | GTX | GTX |
| 8HQ | NGTX | − | − | − | NGTX | |
| 8HQ | NGTX | + | + | + | GTX | |
| Anis | NGTX | + | + | + | GTX | GTX |
| Anis | NGTX | + | + | + | GTX | |
| Anis | NGTX | + | + | + | GTX | |
| NPDhigh | NGTX | − | + | − | NGTX | NGTX |
| NPDhigh | NGTX | − | − | − | NGTX | |
| NPDhigh | NGTX | + | − | + | GTX | |
| PhB | NGTX | + | − | − | NGTX | NGTX |
| PhB | NGTX | − | − | − | NGTX | |
| PhB | NGTX | − | − | − | NGTX | |
| Que | NGTX | − | − | + | NGTX | NGTX |
| Que | NGTX | − | − | − | NGTX | |
| Que | NGTX | − | − | − | NGTX | |

Bold and underlined means that the result of the method of the invention differs from the standard designation.

TABLE 4C

Log2 treatment: control ratios obtained in triplicate experiments with Ames negative compounds.

| | SLC40A1 | PNMA6A | C10orf65/HOGA1 |
|---|---|---|---|
| APAP | 0.057 | −0.186 | 0.057 |
| APAP | 0.056 | 0.414 | 0.049 |
| APAP | −0.052 | −0.062 | −0.002 |
| DES | 0.723 | 0.135 | 0.206 |
| DES | 1.504 | 0.286 | 0.146 |
| DES | 0.717 | 0.203 | 0.516 |
| Phenol | 0.411 | 1.052 | 0.796 |
| Phenol | 0.65 | 0.262 | 0.113 |
| Phenol | 0.921 | 0.831 | 0.209 |
| TBTO | 0.604 | 0.909 | 0.426 |
| TBTO | 1.649 | 0.663 | 0.098 |
| TBTO | 0.208 | 0.456 | 0.858 |
| VitC | 0.972 | 1.027 | 0.333 |
| VitC | 0.225 | 0.378 | 0.348 |
| VitC | 0.125 | 0.642 | 0.42 |
| AA | −0.174 | 0.167 | −0.045 |
| AA | −0.49 | −0.628 | −0.061 |
| AA | 0.007 | 0.562 | 0.002 |
| ampC | −0.175 | −0.201 | −0.152 |
| ampC | −0.326 | −0.493 | −0.096 |
| ampC | 0.068 | 0.251 | −0.089 |
| ASK | −0.348 | 0.264 | 0.014 |
| ASK | −0.221 | 0.161 | −0.015 |
| ASK | 0.08 | −0.677 | 0.083 |
| BDCM | −0.891 | 0.22 | 0.113 |
| BDCM | −0.178 | −0.289 | 0.258 |
| BDCM | −0.017 | −0.185 | 0.086 |
| CAP | −0.607 | 0.312 | 0.203 |
| CAP | −0.032 | −0.168 | 0.223 |
| CAP | 0.265 | −0.165 | 0.138 |
| CCl4 | −0.888 | 0.412 | 0.361 |
| CCl4 | −0.041 | −0.425 | 0.073 |
| CCl4 | −0.185 | −0.14 | −0.083 |
| Cou | −0.215 | 0.073 | −0.481 |
| Cou | −0.309 | 0.081 | −0.483 |
| COU | −0.104 | 0.14 | −0.069 |
| CsA | 0.534 | 0.051 | −0.593 |
| CsA | 0.176 | 0.088 | −0.309 |
| CsA | 0.246 | 0.495 | −0.302 |
| Cur | 0.174 | −0.138 | 0.113 |
| Cur | 0.252 | −0.135 | 0.028 |
| Cur | 0.253 | 0.263 | −0.293 |
| DDT | 0.685 | −0.223 | −0.925 |
| DDT | 0.118 | 0.118 | 0.469 |
| DDT | 0.493 | −0.515 | −0.025 |
| DEPH | 0.249 | −0.264 | −0.364 |
| DEPH | −0.387 | −0.841 | −0.23 |
| DEPH | 0.234 | −0.034 | −0.559 |
| Diclo | −0.32 | 0.018 | −0.235 |
| Diclo | −0.232 | 0.605 | −0.28 |
| Diclo | −0.324 | 0.219 | −0.115 |
| Dman | 0.005 | −0.035 | 0.022 |
| Dman | −0.155 | 0.459 | −0.159 |
| Dman | −0.035 | 0.01 | 0.023 |
| DZN | 0.569 | −0.352 | −1.12 |
| DZN | 0.773 | −0.624 | −0.738 |
| DZN | 1.44 | −0.03 | −1.077 |
| Estradiol | 0.225 | −0.245 | −0.059 |
| Estradiol | 0.157 | −0.333 | 0.15 |
| Estradiol | −0.013 | −0.166 | −0.112 |
| Ethylacrylate | −0.448 | 0.375 | 0.391 |
| Ethylacrylate | 0.634 | 0.243 | 0.429 |
| Ethylacrylate | 0.031 | 0.409 | 0.624 |
| EthylB | −0.23 | 0.313 | −0.18 |
| EthylB | −0.141 | 0.434 | 0.116 |
| EthylB | 0.295 | 0.392 | −0.084 |
| EuG | 0.161 | 0.39 | −0.156 |
| EuG | 0.712 | 0.124 | 0.3 |
| EuG | 0.293 | 0.031 | −0.066 |
| HCH | 0.334 | −0.604 | −0.367 |
| HCH | 0.924 | −0.2 | −0.143 |
| HCH | 0.712 | 0.012 | −0.165 |
| NBZ | −0.497 | 0.457 | 0.501 |
| NBZ | −0.013 | −0.022 | 0.299 |
| NBZ | 0.144 | −0.009 | 0.138 |
| PCP | 0.408 | 0.037 | 0.068 |
| PCP | −0.361 | −0.052 | 0.055 |
| PCP | −0.334 | −0.137 | 0.019 |
| Phen | −0.646 | −0.023 | 0.043 |
| Phen | 0.127 | 0.218 | 0.056 |
| Phen | −0.048 | −0.237 | 0.034 |
| Prog | −0.154 | 0.147 | −0.015 |
| Prog | −0.108 | −0.03 | −0.077 |
| Prog | −0.502 | 0.164 | 0.293 |
| Res | 0.398 | 0.09 | 0.047 |
| Res | −0.212 | −0.624 | 6.45E−05 |
| Res | −0.057 | 0.288 | −0.043 |
| Resorcinol | 0.867 | 0.284 | 0.534 |
| Resorcinol | 1.665 | 0.632 | 0.693 |
| Resorcinol | 0.803 | 0.252 | 1.012 |
| Sim | −0.601 | 0.246 | 0.22 |
| Sim | −0.1 | 0.186 | 0.14 |
| Sim | −0.245 | 0.202 | 0.155 |
| Sulfi | −0.275 | −0.084 | 0.033 |
| Sulfi | 0.384 | −0.08 | −0.287 |
| Sulfi | 0.425 | 0.133 | −0.164 |
| TCDD | 0.169 | −0.041 | −0.107 |
| TCDD | −0.21 | 0.26 | 0.056 |
| TCDD | 0.104 | 0.072 | 0.151 |
| TCE | 0.195 | −0.244 | −0.36 |
| TCE | −0.121 | −0.041 | −0.274 |
| TCE | −0.304 | 0.062 | −0.003 |
| TPA | −0.327 | −0.493 | 0.108 |
| TPA | 1.338 | −0.137 | −0.423 |
| TPA | 0.199 | −0.26 | 0.14 |
| WY | −0.312 | 0.059 | −0.061 |
| WY | −0.393 | −0.515 | −0.158 |
| WY | −0.643 | 1.157 | −0.053 |
| Reference Value | 0.329 | 0.251 | 0.146 |

TABLE 4D

Determination of GTX or NGTX status according to a method of the invention wherein a compound is scored as GTX when at least two out of three genes are above the reference value.

| Compound | Standard | SLC40A1 | PNMA6A | C10orf65/HOGA1 | At least 2/3 genes +? | Average result over three measurements |
|---|---|---|---|---|---|---|
| APAP | GTX | − | − | − | NGTX | NGTX |
| APAP | GTX | − | + | − | NGTX | |
| APAP | GTX | − | − | − | NGTX | |
| DES | GTX | + | − | + | GTX | GTX |
| DES | GTX | + | + | + | GTX | |
| DES | GTX | + | − | + | GTX | |
| Phenol | GTX | + | + | + | GTX | GTX |

TABLE 4D-continued

Determination of GTX or NGTX status according to a method of the invention wherein a compound is scored as GTX when at least two out of three genes are above the reference value.

| Compound | Standard | SLC40A1 | PNMA6A | C10orf65/HOGA1 | At least 2/3 genes +? | Average result over three measurements |
|---|---|---|---|---|---|---|
| Phenol | GTX | + | + | − | GTX | |
| Phenol | GTX | + | + | + | GTX | |
| TBTO | GTX | + | + | + | GTX | GTX |
| TBTO | GTX | + | + | − | GTX | |
| TBTO | GTX | − | + | + | GTX | |
| VitC | GTX | + | + | + | GTX | GTX |
| VitC | GTX | − | + | + | GTX | |
| VitC | GTX | − | + | + | GTX | |
| AA | NGTX | − | − | − | NGTX | NGTX |
| AA | NGTX | − | − | − | NGTX | |
| AA | NGTX | − | + | − | NGTX | |
| ampC | NGTX | − | − | − | NGTX | NGTX |
| ampC | NGTX | − | − | − | NGTX | |
| ampC | NGTX | − | + | − | NGTX | |
| ASK | NGTX | − | + | − | NGTX | NGTX |
| ASK | NGTX | − | − | − | NGTX | |
| ASK | NGTX | − | − | − | NGTX | |
| BDCM | NGTX | − | − | − | NGTX | NGTX |
| BDCM | NGTX | − | − | + | NGTX | |
| BDCM | NGTX | − | − | − | NGTX | |
| CAP | NGTX | − | + | + | GTX | NGTX |
| CAP | NGTX | − | − | + | NGTX | |
| CAP | NGTX | − | − | − | NGTX | |
| CCl4 | NGTX | − | + | + | GTX | NGTX |
| CCl4 | NGTX | − | − | − | NGTX | |
| CCl4 | NGTX | − | − | − | NGTX | |
| Cou | NGTX | − | − | − | NGTX | NGTX |
| Cou | NGTX | − | − | − | NGTX | |
| COU | NGTX | − | − | − | NGTX | |
| CsA | NGTX | + | − | − | NGTX | NGTX |
| CsA | NGTX | − | − | − | NGTX | |
| CsA | NGTX | − | + | − | NGTX | |
| Cur | NGTX | − | − | − | NGTX | NGTX |
| Cur | NGTX | − | − | − | NGTX | |
| Cur | NGTX | − | + | − | NGTX | |
| DDT | NGTX | + | − | − | NGTX | NGTX |
| DDT | NGTX | − | − | + | NGTX | |
| DDT | NGTX | + | − | − | NGTX | |
| DEPH | NGTX | − | − | − | NGTX | NGTX |
| DEPH | NGTX | − | − | − | NGTX | |
| DEPH | NGTX | − | − | − | NGTX | |
| Diclo | NGTX | − | − | − | NGTX | NGTX |
| Diclo | NGTX | − | + | − | NGTX | |
| Diclo | NGTX | − | − | − | NGTX | |
| Dman | NGTX | − | − | − | NGTX | NGTX |
| Dman | NGTX | − | + | − | NGTX | |
| Dman | NGTX | − | − | − | NGTX | |
| DZN | NGTX | + | − | − | NGTX | NGTX |
| DZN | NGTX | + | − | − | NGTX | |
| DZN | NGTX | + | − | − | NGTX | |
| Estradiol | NGTX | − | − | − | NGTX | NGTX |
| Estradiol | NGTX | − | − | + | NGTX | |
| Estradiol | NGTX | − | − | − | NGTX | |
| Ethylacrylate | NGTX | − | + | + | GTX | GTX |
| Ethylacrylate | NGTX | + | − | + | GTX | |
| Ethylacrylate | NGTX | − | + | + | GTX | |
| EthylB | NGTX | − | + | − | NGTX | NGTX |
| EthylB | NGTX | − | + | − | NGTX | |
| EthylB | NGTX | − | + | − | NGTX | |
| EuG | NGTX | − | + | − | NGTX | NGTX |
| EuG | NGTX | + | − | + | GTX | |
| EuG | NGTX | − | − | − | NGTX | |
| HCH | NGTX | + | − | − | NGTX | NGTX |
| HCH | NGTX | + | − | − | NGTX | |
| HCH | NGTX | + | − | − | NGTX | |
| NBZ | NGTX | − | + | + | GTX | NGTX |
| NBZ | NGTX | − | − | + | NGTX | |
| NBZ | NGTX | − | − | − | NGTX | |
| PCP | NGTX | + | − | − | NGTX | NGTX |
| PCP | NGTX | − | − | − | NGTX | |
| PCP | NGTX | − | − | − | NGTX | |
| Phen | NGTX | − | − | − | NGTX | NGTX |
| Phen | NGTX | − | − | − | NGTX | |

TABLE 4D-continued

Determination of GTX or NGTX status according to a method of the invention wherein a compound is scored as GTX when at least two out of three genes are above the reference value.

| Compound | Standard | SLC40A1 | PNMA6A | C10orf65/HOGA1 | At least 2/3 genes +? | Average result over three measurements |
|---|---|---|---|---|---|---|
| Phen | NGTX | − | − | − | NGTX | |
| Prog | NGTX | − | − | − | NGTX | NGTX |
| Prog | NGTX | − | − | − | NGTX | |
| Prog | NGTX | − | − | + | NGTX | |
| Res | NGTX | + | − | − | NGTX | NGTX |
| Res | NGTX | − | − | − | NGTX | |
| Res | NGTX | − | + | − | NGTX | |
| Resorcinol | NGTX | + | + | + | GTX | GTX |
| Resorcinol | NGTX | + | + | + | GTX | |
| Resorcinol | NGTX | + | + | + | GTX | |
| Sim | NGTX | − | − | + | NGTX | NGTX |
| Sim | NGTX | − | − | − | NGTX | |
| Sim | NGTX | − | − | + | NGTX | |
| Sulfi | NGTX | − | − | − | NGTX | NGTX |
| Sulfi | NGTX | + | − | − | NGTX | |
| Sulfi | NGTX | + | − | − | NGTX | |
| TCDD | NGTX | − | − | − | NGTX | NGTX |
| TCDD | NGTX | − | + | − | NGTX | |
| TCDD | NGTX | − | − | + | NGTX | |
| TCE | NGTX | − | − | − | NGTX | NGTX |
| TCE | NGTX | − | − | − | NGTX | |
| TCE | NGTX | − | − | − | NGTX | |
| TPA | NGTX | − | − | − | NGTX | NGTX |
| TPA | NGTX | + | − | − | NGTX | |
| TPA | NGTX | − | − | − | NGTX | |
| WY | NGTX | − | − | − | NGTX | NGTX |
| WY | NGTX | − | − | − | NGTX | |
| WY | NGTX | − | + | − | NGTX | |

Bold and underlined means that the result of the method of the invention differs from the standard designation.

An important increase of the specificity, and therewith a reduction of the false positive results, of up to 32% is achieved when the method according to the invention is compared to the outcome of the conventional in vitro assays.

The false positive rate of the conventional in vitro assays exceeds 50%, with the exception of Ames (23%) (7), whereas the false-positive rate of the method according to the invention is approximately 16%.

The false positive rate of our assay results from the misclassification of 5 NGTX compounds, namely RR, 2-Cl, PhB, Anis and Sim. All of these compounds, with the exception of Sim, have delivered positive results in the conventional in vitro genotoxicity assays (see Table 5).

Due to its high accuracy, and especially due to its high specificity, the method according to the invention may be used in several applications in order to avoid unnecessary experiments on animals. For instance, it may facilitate the hazard identification of existing industrial chemicals to serve the purposes of the EU chemical policy program REACH, for which it has been estimated that some 400,000 rodents may be used for testing genotoxicity in vivo (14); specifically, chemical prioritization by grouping chemicals for further testing for genotoxicity in vivo may be supported.

The method according to the invention may also be applied for assessing genotoxic properties of novel cosmetics, since in the EU, for cosmetic ingredients, animal testing is generally prohibited since 2009 (EC Regulation 1223/2009). Furthermore, our approach may be effective in drug development, by significantly avoiding false positive results of the standard in vitro genotoxicity test battery, implying that promising lead compounds will no longer be eliminated due to wrong assumptions on their genotoxic properties and that rodents would not be unnecessarily sacrificed in costly experimentation.

EXAMPLES

Example 1: Chemicals

Table 5 shows the doses for the 62 compounds used in this study and provides information on the stratification of the compounds based on the Ames assay, and on in vivo genotoxicity data.

TABLE 5

Chemicals used in this study, selected doses and information on in vitro and in vivo genotoxicity data.

| Compound | Abbreviation | CAS no | Dose | Solvent | Ames | In vitro GTX | In vivo GTX |
|---|---|---|---|---|---|---|---|
| 2-acetyl aminofluorene | 2AAF | 53-96-3 | 50 µM | DMSO | + | + | + |
| Aflatoxin B1 | AFB1 | 1162-65-8 | 1 µM | DMSO | + | + | + |
| Benzo[a]pyere | BaP | 50-32-8 | 2 µM | DMSO | + | + | + |

TABLE 5-continued

Chemicals used in this study, selected doses and information on in vitro and in vivo genotoxicity data.

| Compound | Abbreviation | CAS no | Dose | Solvent | Ames | In vitro GTX | In vivo GTX |
|---|---|---|---|---|---|---|---|
| 7,12-Dimethyl benzantracene | DMBA | 57-97-6 | 5 µM | DMSO | + | + | + |
| Dimethyl nitrosamine | DMN | 62-75-9 | 2 mM | DMSO | + | + | + |
| Mitomycine C | MMC | 50-07-7 | 200 nM | DMSO | + | + | + |
| Para-cresidine | pCres | 120-71-8 | 2 mM | EtOH | + | + | + |
| 2-(chloromethyl)pyridine•HCl | 2CMP | 6959-47-3 | 300 µM | DMSO | + | + | − |
| 4-acetyl aminofluorene | 4AAF | 28322-02-3 | 100 nM | DMSO | + | + | − |
| 4-Nitro-o-phenylenediamine | NPD | 99-56-9 | 2 mM | DMSO | + | + | − |
| 8-quinolinol | 8HQ | 148-24-3 | 15 µM | DMSO | + | + | − |
| Quercetin | Que | 117-39-5 | 50 µM | DMSO | + | + | − |
| Phenobarbital | PhB | 50-06-6 | 1 mM | DMSO | + | + | − |
| Acetaminophen | APAP | 103-90-2 | 100 µM | PBS | − | + | + |
| Diethylstilbestrol | DES | 56-53-1 | 5 µM | EtOH | − | + | + |
| Phenol | Ph | 108-95-2 | 2 mM | DMSO | − | + | + |
| Tributylinoxide | TBTO | 56-35-9 | 0.02 nM | EtOH | − | + | + |
| Curcumin | Cur | 458-37-7 | 1 µM | DMSO | − | + | − |
| o-anthranilic acid | AnAc | 118-92-3 | 2 mM | DMSO | − | + | − |
| Resorcinol | RR | 108-46-3 | 2 mM | EtOH | − | + | − |
| Sulfisoxazole | Sulfi | 127-69-5 | 5 µM | DMSO | − | + | − |
| 17beta-estradiol | E2 | 50-28-2 | 30 µM | DMSO | − | + | − |
| Ethylacrylate | EtAc | 140-88-5 | 1 mM | EtOH | − | + | − |
| Phenacetin | Phen | 62-44-2 | 1 mM | EtOH | − | + | − |
| L-ascorbic acid | VitC | 50-81-7 | 2 mM | PBS | − | − | + |
| Ampicillin trihydrate | AmpC | 7177-48-2 | 250 µM | DMSO | − | − | − |
| Diclofenac | Diclo | 15307-86-5 | 100 µM | PBS | − | − | − |
| D-mannitol | Dman | 69-65-8 | 250 µM | PBS | − | − | − |
| Cyclosporine A | CsA | 59865-13-3 | 3 µM | DMSO | − | − | − |
| di(2-ethylhexyl)phthalate | DEHP | 117-81-7 | 10 mM | DMSO | − | − | − |
| Reserpine | Res | 50-55-5 | 12.5 µM | DMSO | − | − | − |
| 2,3,7,8-tetrachloro dibenzo-p-dioxin | TCDD | 1746-01-6 | 10 nM | DMSO | − | − | − |
| Tetradecanoyl phorbol acetate | TPA | 16561-29-8 | 500 nM | DMSO | − | − | − |
| Wy 14643 | Wy | 50892-23-4 | 200 µM | DMSO | − | − | − |
| 4-aminobiphenyl | ABP | 92-67-1 | 80 µM | DMSO | + | + | + |
| Azathioprine | AZA | 446-86-6 | 250 µM | DMSO | + | + | + |
| Benzidine | BZ | 92-87-5 | 1 mM | DMSO | + | + | + |
| Chlorambucil | Cb | 305-03-3 | 20 µM | DMSO | + | + | + |
| Cisplatin | cisPt | 15663-27-1 | 20 µM | PBS | + | + | + |
| Cyclophosphamide | CP | 6055-19-2 | 2 mM | PBS | + | + | + |
| Diethylnitrosamine | DEN | 55-18-5 | 500 µM | DMSO | + | + | + |
| 1-ethyl-1-nitrosourea | ENU | 759-73-9 | 1 mM | DMSO | + | + | + |
| Furan | Fu | 110-00-9 | 2 mM | DMSO | + | + | + |
| 2-amino-3-methyimidazo[4,5-f]quinoline | IQ | 76180-96-6 | 800 µM | DMSO | + | + | + |
| 4,4'-methylenebis(2-chloroaniline) | MOCA | 101-14-4 | 60 µM | DMSO | + | + | + |
| 2-chloroethanol | 2-Cl | 107-07-3 | 2 mM | DMSO | + | + | − |
| p-anisidine | Anis | 104-94-9 | 60 µM | DMSO | + | + | − |
| Bromodichloro methane | BDCM | 75-27-4 | 2 mM | DMSO | − | + | − |
| Carbon tetrachloride | CCl4 | 56-23-5 | 2 mM | DMSO | − | + | − |
| Ethylbenzene | EthylB | 100-41-4 | 800 µM | DMSO | − | + | − |
| Eugenol | EuG | 97-53-0 | 500 µM | DMSO | − | + | − |
| Nitrobenzene | NBZ | 98-95-3 | 2 mM | DMSO | − | − | − |
| 1,1,1-trichloro-2,2-di-(4-chlorophenyl)ethane | DDT | 50-29-3 | 80 µM | DMSO | − | − | − |
| Pentachlorophenol | PCP | 87-86-5 | 10 µM | EtOH | − | − | − |
| Progesterone | Prog | 57-83-0 | 6 µM | EtOH | − | − | − |
| Tetrachloroethylene | TCE | 127-18-4 | 2 mM | EtOH | − | − | − |

TABLE 5-continued

Chemicals used in this study, selected doses and information on in vitro and in vivo genotoxicity data.

| Compound | Abbreviation | CAS no | Dose | Solvent | Ames | In vitro GTX | In vivo GTX |
|---|---|---|---|---|---|---|---|
| Lindane | γ-HCH | 58-89-9 | 2 mM | DMSO | − | − | − |
| Acesulfame-K | ASK | 55589-62-3 | 2 mM | DMSO | − | − | − |
| Caprolactam | CAP | 105-60-2 | 2 mM | DMSO | − | − | − |
| Coumaphos | COU | 56-72-4 | 250 μM | DMSO | − | − | − |
| Diazinon | DZN | 333-41-5 | 250 μM | DMSO | − | − | − |
| Simazine | Sim | 122-34-9 | 50 μM | DMSO | − | − | − |

*Ames results based on NTP data
† in vitro genotoxicity is considered positive when at least one in vitro genotoxicity assay (Ames, MN, CA, MLA) showed positive results,
‡ in vivo genotoxicity is considered positive when at least one in vivo genotoxicity assays (MN, CA) showed positive results. Equivocal in vivo data are considered positive.

Example 2: Cell Culture and Treatment

HepG2 cells were cultured in 6-well plates as previously described (15). When the cells were 80% confluent, medium was replaced with fresh medium containing the corresponding dose of each compound or with the corresponding control treatment (DMSO, EtOH, or PBS 0.5%).

All doses were selected based on a MTT assay resulting to 80% viability at 72 h incubation, or a maximum dose of 2 mM was used when no cytotoxicity was observed, or the maximum soluble dose was used, whichever is the lowest (15). Cells were exposed for 24 h. These exposure periods were selected based on the time that GTX need to be metabolized (15) and the cell cycle duration of HepG2 cells (approximately 20 h) (16). Thereafter the culture medium was replaced by TRIZOL (Gibco/BRL) for RNA isolation. Three independent biological replicates were conducted.

Example 3: Total RNA Isolation and Microarray Experiments

Total RNA was extracted using 0.5 ml TRIZOL according to the manufacturer's instructions and purified using RNeasy® Mini Kits (Qiagen). Sample preparation, hybridization, washing, staining and scanning of the Affymetrix Human Genome U133 Plus 2.0 GeneChip arrays were conducted according to the manufacturer's protocol as previously described (17). Quality controls were within acceptable limits. Hybridization controls were called present on all arrays and yielded the expected increases in intensities.

Example 4: Annotation and Normalization of Microarray Data

The obtained data sets were re-annotated to the MBNI Custom CDF-files versions 11 and 14. (http://brainarray.mbni.med.umich.edu/Brainarray/Database/CustomCDF/genomic_curated_CDF.asp) (18) and RMA normalized (19) using the NuGOExpressionFileCreator in GenePattern (20). Log 2 ratios were calculated for each replicate to the corresponding control treatment.

Example 5: Selection of Classifiers for Genotoxicity

The 34 chemicals were stratified into two groups based on the results of the Ames mutagenicity assay (Table 5) and consequently assigned to Ames-positive and Ames-negative. Within each group both in vivo GTX and in vivo NGTX chemicals are present. For the Ames-positive group, 13 t-tests were performed to select classifiers for discriminating in vivo GTX compounds from in vivo NGTX compounds. Genes significant in all t-tests were then selected. Within this geneset, sub-sets were investigated with regards to their predictive power. The best prediction was obtained for the geneset with three genes, namely NR0B2, PWWP2B, and LOC100131914.

For the Ames-negative group 21 t-tests were performed to select classifiers for discriminating in vivo GTX from in vivo NGTX chemicals. Genes significant in all t-tests were then selected. Within this geneset, sub-sets were investigated with regards to their predictive power. The best prediction was obtained for the geneset with three genes, namely SLC40A1, PNMA6A and C10orf65.

Example 6: Class Prediction of the Training and Validation Sets of Reference Compounds Prediction analysis according to our method was conducted for each of the selected genesets. The gene expression data of the three replicates was compared to the respective reference values. A compound was predicted to be in vivo GTX or in vivo non-GTX when at least two out of the three replicates were assigned to one class.

The accuracy was calculated as the percentage of the correctly classified chemicals to the total number of tested chemicals; the sensitivity as the percentage of the correctly classified GTX to the total number of tested GTX compounds and the specificity as the percentage of the correctly classified NGTX to the total number of tested NGTX compounds.

REFERENCES

1. Jemal A, Siegel R, Xu J, Ward E. Cancer statistics, 2010. CA Cancer J Clin. 2010 September-October; 60(5):277-300.
2. OECD. Mortality from Cancer, in OECD, Health at a Glance: Europe 2010 OECD Publishing. 2010 34-5.
3. Petrucelli N, Daly M B, Feldman G L. Hereditary breast and ovarian cancer due to mutations in BRCA1 and BRCA2. Genet Med. 2010 May; 12(5):245-59.
4. Clapp R W, Jacobs M M, Loechler E L. Environmental and occupational causes of cancer: new evidence 2005-2007. Rev Environ Health. 2008 January-March; 23(1):1-37.

5. Oliveira P A, Colaco A, Chaves R, Guedes-Pinto H, De-La-Cruz P L, Lopes C. Chemical carcinogenesis. An Acad Bras Cienc. 2007 December; 79(4):593-616.
6. Ames B N, Lee F D, Durston W E. An improved bacterial test system for the detection and classification of mutagens and carcinogens. Proc Natl Acad Sci USA. 1973 March; 70(3):782-6.
7. Kirkland D, Aardema M, Henderson L, Müller L. Evaluation of the ability of a battery of three in vitro genotoxicity tests to discriminate rodent carcinogens and non-carcinogens I. Sensitivity, specificity and relative predictivity. Mutat Res. 2005 Jul. 4; 584(1-2):1-256.
8. ICH. Guidance on genotoxicity testing and data interpretation for pharmaceuticals intended for human use S2(R1). 2008.
9. IARC. IARC Monographs on the Evaluation of Carcinogenic Risks to Humans. Supplement 7: Overall Evaluations of Carcinogenicity: An Updating of IARC Monographs Volumes 1 to 42. 1987.
10. IARC. IARC Monographs on the evaluation of carcinogenic risks to humans. Volume 73: Some Chemicals that Cause Tumours of the Kidney or Urinary Bladder in Rodents and Some Other Substances. 1999.
11. Voogd C E. Azathioprine, a genotoxic agent to be considered non-genotoxic in man. Mutat Res. 1989 September; 221(2):133-52.
12. Bergman K, Muller L, Teigen S W. Series: current issues in mutagenesis and carcinogenesis, No. 65. The genotoxicity and carcinogenicity of paracetamol: a regulatory (re)view. Mutat Res. 1996 Feb. 1; 349(2):263-88.
13. Nagafuchi K, Miyazaki K. Modulation of genotoxicity of azathioprine by intracellular glutathione in hepatocytes. J Cancer Res Clin Oncol. 1991; 117(4):321-5.
14. van derJagt K, Munn S, Tørsløv J, Bruijn Jd. Alternative Approaches can reduce the use of test animals under REACH: Addendum to the report "Assessment of additional testing needs under REACH. Effects of (Q)SARS, risk based testing and voluntary industry initiatives". EUROPEAN COMMISSION, DIRECTORATE GENERAL JRC, JOINT RESEARCH CENTRE, Institute for Health and Consumer Protection. 2004 November.
15. Jennen D G, Magkoufopoulou C, Ketelslegers H B, van Herwijnen M H, Kleinjans J C, van Delft J H. Comparison of HepG2 and HepaRG by whole genome gene expression analysis for the purpose of chemical hazard identification. Toxicol Sci. 2010 Jan. 27.
16. Knasmüller S, Parzefall W, Sanyal R, Ecker S, Schwab C, Uhl M, et al. Use of metabolically competent human hepatoma cells for the detection of mutagens and antimutagens. Mutat Res 1998 Jun. 18; 402(1-2):185-202.
17. Jennen D G, Magkoufopoulou C, Ketelslegers H B, van Herwijnen M H, Kleinjans J C, van Delft J H. Comparison of HepG2 and HepaRG by whole genome gene expression analysis for the purpose of chemical hazard identification. Toxicol Sci. January 27.
18. Dai M, Wang P, Boyd A D, Kostov G, Athey B, Jones E G, et al. Evolving gene/transcript definitions significantly alter the interpretation of GeneChip data. Nucleic Acids Res. 2005; 33(20):e175.
19. Irizarry R A, Hobbs B, Collin F, Beazer-Barclay Y D, Antonellis K J, Scherf U, et al. Exploration, normalization, and summaries of high density oligonucleotide array probe level data. Biostatistics. 2003 April; 4(2):249-64.
20. De Groot P J, Reiff C, Mayer C, Muller M. NuGO contributions to GenePattern. Genes Nutr. 2008 December; 3(3-4):143-6.

The invention claimed is:

1. A method of gene expression profiling, the method comprising:
exposing a HepG2 cell to a compound for a period of time between 12 and 48 hours,
processing the exposed HepG2 cell to produce a cell extract comprising mRNA;
measuring a level of mRNA in the cell extract for each of the members of a first gene set comprising at least genes NR0B2, PWWP2B and LOC100131914, or
measuring a level of mRNA for each of the members of a second gene set, comprising at least genes SLC40A1, PNMA6A and C10orf65.

2. The method according to claim 1, wherein the first gene set further comprises at least one gene selected from the group consisting of genes CEACAM1, SLC27A1, TTR, UBE2E2, NAT8, GMFG, RBPMS, C10orf10, PROSC, TBC1D9, OR10H1, APOM, C1orf128, AVEN, ZNRF3 and SNORD8.

3. The method according to claim 1, wherein the second gene set further comprises at least one gene selected from the group consisting of genes SGK1, SLC64A, ANXA6, BTD, FGA, NDUFA10, NFATC3, MTMR15, ANAPC5, ZNF767, SCRN2 and GSTK1.

4. The method according to claim 1, wherein said period of time is about 24 hours.

5. A method of measuring gene expression performing quantitative PCR, the method comprising:
exposing a HepG2 cell to a compound for a period of time between 12 and 48 hours,
producing a cell extract comprising mRNA from the exposed HepG2 cell; and
performing quantitative PCR on the cell extract for the members of a first gene set comprising at least genes NR0B2, PWWP2B and LOC100131914 and/or a second gene set comprising at least genes SLC40A1, PNMA6A and C10orf65.

* * * * *

UNITED STATES PATENT AND TRADEMARK OFFICE
CERTIFICATE OF CORRECTION

PATENT NO. : 9,822,414 B2
APPLICATION NO. : 14/117731
DATED : November 21, 2017
INVENTOR(S) : Van Delft et al.

It is certified that error appears in the above-identified patent and that said Letters Patent is hereby corrected as shown below:

In the Claims

Claim 5, Column 24, Line 41, change "of measuring gene expression performing" to --of performing--

Signed and Sealed this
Twenty-fourth Day of July, 2018

Andrei Iancu
*Director of the United States Patent and Trademark Office*